United States Patent
Schwab et al.

(10) Patent No.: US 9,763,870 B2
(45) Date of Patent: Sep. 19, 2017

(54) FORMULATION COMPRISING LIQUID ESTER QUATS AND/OR IMIDAZOLINIUM SALTS AND POLYMER THICKENERS

(71) Applicant: Evonik Degussa GmbH, Essen (DE)

(72) Inventors: Peter Schwab, Essen (DE); Ursula Westerholt, Essen (DE); Uta Kortemeier, Essen (DE); Jochen Kleinen, Heinsberg (DE); Christian Hartung, Essen (DE); Hans-Juergen Koehle, Mainhausen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/861,380

(22) Filed: Sep. 22, 2015

(65) Prior Publication Data

US 2016/0081907 A1  Mar. 24, 2016

(30) Foreign Application Priority Data

Sep. 22, 2014  (EP) .................................. 14185779

(51) Int. Cl.
| | | |
|---|---|---|
| A61K 31/4164 | (2006.01) | |
| A61K 31/121 | (2006.01) | |
| A61K 8/81 | (2006.01) | |
| A61K 8/41 | (2006.01) | |
| A61K 8/49 | (2006.01) | |
| A61Q 5/12 | (2006.01) | |
| A61K 8/73 | (2006.01) | |

(52) U.S. Cl.
CPC ............ *A61K 8/8152* (2013.01); *A61K 8/416* (2013.01); *A61K 8/4946* (2013.01); *A61K 8/73* (2013.01); *A61K 8/731* (2013.01); *A61K 8/8147* (2013.01); *A61Q 5/12* (2013.01); *A61K 2800/805* (2013.01)

(58) Field of Classification Search
CPC . A61K 31/415; A61K 31/4164; A61K 31/121
USPC ................................................ 514/399, 676
See application file for complete search history.

(56) References Cited

U.S. PATENT DOCUMENTS

| | | |
|---|---|---|
| 5,180,508 A | 1/1993 | Birkhan et al. |
| 5,364,542 A | 11/1994 | Birkhan et al. |
| 5,464,565 A | 11/1995 | Hamann et al. |
| 5,681,972 A | 10/1997 | Hamann et al. |
| 5,718,891 A | 2/1998 | Prat et al. |
| 5,962,708 A | 10/1999 | Hamann et al. |
| 6,110,887 A | 8/2000 | Euler et al. |
| 6,180,593 B1 | 1/2001 | Fender et al. |
| 6,180,594 B1 | 1/2001 | Fender et al. |
| 6,376,455 B1 | 4/2002 | Friedli et al. |
| 6,653,275 B1 | 11/2003 | Fender et al. |
| 7,074,419 B2 | 7/2006 | Dietz et al. |
| 7,578,857 B1 | 8/2009 | Massoni |
| 8,211,972 B2 | 7/2012 | Meyer et al. |
| 8,563,499 B2 | 10/2013 | Kohle et al. |
| 8,569,224 B2 | 10/2013 | Kohle et al. |
| 8,778,319 B2 | 7/2014 | Herrwerth et al. |
| 8,883,712 B2 | 11/2014 | Kohle et al. |
| 9,073,818 B2 | 7/2015 | Herrwerth et al. |
| 2004/0005286 A1 | 1/2004 | Giroud |
| 2004/0258651 A1 | 12/2004 | Pascaly et al. |
| 2006/0140899 A1 | 6/2006 | Koenig et al. |
| 2009/0170734 A1 | 7/2009 | Schwab et al. |
| 2013/0071343 A1 | 3/2013 | Herrwerth et al. |
| 2013/0171087 A1 | 7/2013 | Herrwerth et al. |
| 2013/0225470 A1 | 8/2013 | Allen et al. |
| 2014/0286889 A1 | 9/2014 | Koehle et al. |
| 2015/0203443 A1 | 7/2015 | Klostermann et al. |

FOREIGN PATENT DOCUMENTS

| | | |
|---|---|---|
| DE | 4308794 C1 | 4/1994 |
| DE | 10327871 A1 | 1/2005 |
| DE | 102008001788 | 11/2009 |
| DE | 102012205088 A1 | 10/2013 |
| EP | 0483195 | 5/1992 |
| EP | 0581442 * | 2/1994 |
| EP | 0581442 A2 | 2/1994 |
| EP | 1125574 B1 | 6/2005 |
| EP | 2168564 A2 | 3/2010 |
| EP | 2783677 A2 | 10/2014 |
| WO | WO9101295 | 2/1991 |
| WO | WO2004112731 | 12/2004 |
| WO | WO2006034992 | 4/2006 |
| WO | WO2008092676 A1 | 8/2008 |
| WO | WO2009138306 A1 | 11/2009 |

OTHER PUBLICATIONS

"Ullmanns Encyklopädie der technischen Chemie", vol. 19, Verlag Chemie Weinheim, Feb. 1980, pp. 233-263.
Shapiro, I., et al., "Environmentally Friendly Ester Quats", Cosmetics and Toiletries Magazine, Dec. 1994, vol. 109, pp. 77-80.
Brock, M., et al., "Neue Entwicklungen auf dem Gebiet der Waescheweichspueler", Tens. Surf. Det., 30, pp. 394-399, 1993, English language abstract only.
Lagerman, R., et al. "Synthesis and Performance of Ester Quaternary Biodegradable Softners", JAOCS, Jan. 1994, pp. 97-100, vol. 71, No. 1.
Puchta, R., et al., "A New Generation of Softners", Tenside Surf. Det. 30, May 1993, 3, pp. 186-191.
Schrader, K. et al., "Grundlagen und Rezepturen der Kosmetika" ["Principles and Formulations of Cosmetics"], 1989, 2nd edition, p. 329 to 341, Hüthig Buch Verlag Heidelberg.

* cited by examiner

*Primary Examiner* — Yong Chu
*Assistant Examiner* — Sonya Wright
(74) *Attorney, Agent, or Firm* — Scully, Scott, Murphy & Presser, P.C.

(57) ABSTRACT

The invention relates to formulations containing liquid ester quats and/or imidazolinium salts and polymer thickeners and to the use thereof.

13 Claims, No Drawings

FORMULATION COMPRISING LIQUID ESTER QUATS AND/OR IMIDAZOLINIUM SALTS AND POLYMER THICKENERS

FIELD OF THE INVENTION

The invention relates to formulations comprising liquid ester quats and polymer thickeners and to the use thereof.

BACKGROUND OF THE INVENTION

Hair conditioning formulations based on liquid ester quats and/or imidazolinium salts are characterized by excellent conditioning properties and ease of use and versatility. However, the long-term stability of simple formulations compared to solid ester quats and/or imidazolinium salts is lacking. Emulsion stabilization is problematic.

U.S. Pat. No. 6,376,455 discloses in example 7 a formulation comprising hydroxyethylcellulose and a quaternized esterification product of methylethylisopropanolamine. Reproductions reveal that the ester quat used has a melting point of at least 85° C. at 1 bar.

SUMMARY OF THE INVENTION

The present invention provides storage-stable formulations comprising ester quats and/or imidazolinium salts.

It has now been found, surprisingly, by the Applicant of the present invention that formulations comprising liquid ester quats and/or imidazolinium salts can be made stable for over a long term by addition of carbomers or other polymers. This is particularly surprising in the case of carbomers since carbomers normally lead to phase separations due to interaction with cationic surfactants and therefore carbomers cannot currently be used in hair conditioning formulations.

The present invention therefore relates to formulations comprising:
  at least one liquid ester quat and/or at least one liquid imidazolinium salt (component A)); and
  at least one polymer thickener (component B)).

The invention further relates to the use of the formulations according to the invention in cosmetic and also textile applications.

One advantage of the present invention is that the ester quats and/or imidazolinium salts used are liquid at room temperature and thus they can be easily incorporated into a final consumer formulation without the use of solvents, as a result of which such a solvent does not necessarily have to be present in said formulation.

A further advantage of the present invention is that the shine of the treated keratin fibres is increased.

A further advantage of the present invention is that the compounds used develop a good effect even in small use amounts.

It is a further advantage that the compounds used have little impact from an ecological point of view.

It is a further advantage that the formulations according to the invention exhibit an improved conditioning effect on keratin fibres with longer rinse-off times than quaternary ester compounds known hitherto.

A further advantage of the present invention is that ester quats have increased hydrolysis stability in the formulation.

A further advantage of the present invention is that they do not crystallize out.

A further advantage of the present invention is that they are effective in relatively low use concentrations.

A further advantage of the present invention is that the formulations according to the invention protect hair colorants from being washed out.

A further advantage of the present invention is that the formulations according to the invention protect keratin fibres against thermally induced damage.

A further advantage of the present invention is that the formulations according to the invention reduce the combing forces on wet and dry hair.

A further advantage of the present invention is that the formulations according to the invention can be made methanol-free.

A further advantage of the present invention is that the formulations according to the invention are particularly economic.

DETAILED DESCRIPTION OF THE INVENTION

The term "ester quat" in the context of the present invention is understood to mean a chemical compound comprising both a quaternary nitrogen atom and an ester bond in the cationic part of an ion pair. This is preferably understood to mean a class of surface-active quaternary ammonium compounds having the general formula $R_{11}R_{12}R_{13}R_{14}N+X-$, wherein at least one of the residues $R_{11}$ to $R_{14}$ has more than 4 carbon atoms and is bonded to the charged group via ester bonds C(O)O— or OC(O)—, and X— is understood to mean any anionic counterion.

The following represent definitions for the residues $R_{11}$ to $R_{14}$:

$R_{11}$ is a divalent, saturated or unsaturated, straight-chain, branched or cyclic, optionally substituted hydrocarbon residue and optionally interrupted by oxygen atoms, nitrogen atoms or carboxyl groups $R_{12}$ is a divalent, saturated or unsaturated, straight-chain, branched or cyclic, optionally substituted hydrocarbon residue and optionally interrupted by oxygen atoms, nitrogen atoms or carboxyl groups $R_{13}$ is a divalent, saturated or unsaturated, straight-chain, branched or cyclic, optionally substituted hydrocarbon residue and optionally interrupted by oxygen atoms, nitrogen atoms or carboxyl groups $R_{14}$ is a divalent, saturated or unsaturated, straight-chain, branched or cyclic, optionally substituted hydrocarbon residue and optionally interrupted by oxygen atoms, nitrogen atoms or carboxyl groups.

The term "liquid ester quats" in the context of the present invention is understood to mean ester quats having, at 1 bar, a melting point of 60° C. or lower, preferably 40° C. and lower, particularly preferably 25° C. or lower and especially preferably 10° C. or lower. If the ester quats present in the formulation are mixtures of ester quats, the melting point relates to the melting point of the mixture of all the ester quats present in the formulation. The same applies to imidazolinium salts, to fatty alcohols and emulsifiers.

The term "polymer thickener" in the context of the present invention is understood to mean polymers which can significantly increase the viscosity of aqueous phases.

Unless otherwise stated, all percentages (%) given are percentages by weight.

The quaternized fatty acid alcohol amine esters used in the context of the invention can be prepared by relevant methods of preparative organic chemistry. Usually, the preparation of ester quats is based on a multistage process in which the esterified alkanolamine is prepared by first reacting an alkanolamine with carboxylic acids or corresponding derivatives, and said alkanolamine is then subsequently quaternized with a suitable reagent.

For suitable preparation processes, reference may be made to EP0483195, according to which trialkanolamine is partially esterified in the presence of hypophosphorous acid with fatty acids, air is passed through and then quaternization is carried out with dimethyl sulphate or ethylene oxide. The compounds listed therein serve as plasticizers for textiles. DE4308794 describes the preparation of ester quats by carrying out the quaternization of the triethanolamine esters in the presence of suitable dispersants. Overviews of these topics can be found, for example under R. Puchta et al. in Tens. Surf. Det., 30, 186 (1993), M. Brock in Tens. Surf. Det., 30, 394 (1993), R. Lagerman et al. in J. Am. Chem. Soc., 71, 97 (1994) or under I. Shapiro in Cosm. Toil., 109, 77 (1994).

Liquid ester quats contained in the formulation according to the invention are preferably selected from the group of quaternized fatty acid alkanolamine ester salts, particularly preferably from the groups of quaternized fatty acid ethanolamine ester salts and quaternized fatty acid isopropanolamine ester salts and mixtures thereof, especially preferably from the group of quaternized fatty acid isopropanolamine ester salts based on dimethylmonoisopropanolamine, methyldiisopropanolamine or triisopropanolamine.

Liquid ester quats contained in the formulation according to the invention particularly preferably comprise at least one compound of general formula I)

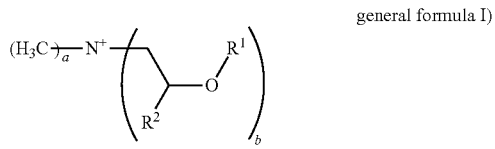

general formula I)

where $R^1$ is an acyl residue of an at least monounsaturated fatty acid having a chain length of 18 to 24 carbon atoms or the acyl residue of isostearic acid or ricinoleic acid,
where $R^2$ is an alkyl residue having 1 to 6 carbon atoms, preferably methyl, ethyl, propyl or isopropyl, particularly preferably methyl,
where a=1 to 3 and b=1 to 3, preferably a=1.7 to 2.3 and b=1.7 to 2.3
with the proviso that a+b=4.

If b is >1, the residues $R^1$ can be identical or different.

$R^1$ as acyl residue of an at least monounsaturated fatty acid with a chain length from 18 to 24 carbon atoms can contain one or more, for example two or three, double bonds.

Preferred formulations according to the invention are characterized in that $R^1$ as acyl residue of an at least monounsaturated fatty acid with a chain length of 18 to 24 carbon atoms is selected from the acyl residues of the acids from the group of oleic acid, elaidic acid, vaccenic acid, gadoleic acid, icosenoic acid, cetoleic acid, erucic acid, nervonic acid, linolic acid, alpha-linolenic acid, gamma-linolenic acid, calendulic acid, punicic acid, alpha-elaeostearic acid, beta-elaeostearic acid, arachidonic acid, timnodonic acid, clupanodonic acid and cervonic acid, wherein oleic acid is particularly preferred.

According to the invention, it is also possible to use mixtures of these carboxylic acids.

Preferred formulations comprise at least one compound of the general formula I) where a=1.7 to 2.3 and b=1.7 to 2.3, particularly preferably a=b=2.

A particularly preferred formulation according to the invention is characterized in that $R^1$ is the acyl residue of oleic acid and a=1.7 to 2.3 and b=1.7 to 2.3, particularly preferably a=b=2.

In the formulation according to the invention, besides a compound of the general formula I), further compounds may be present which, apart from the residue $R^1$, correspond to the compound of the general formula I), i.e. the analogous residue $R^{1a}$ is the acyl residue of another carboxylic acid, in particular of another fatty acid.

Thus, in addition to the compound of the general formula I), at least one compound of general formula Ia) can also be present

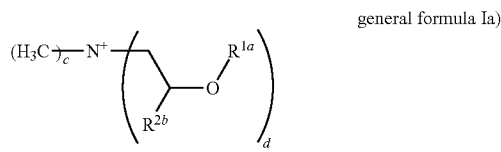

general formula Ia)

where $R^{1a}$ is an acyl residue of a carboxylic acid different from the carboxylic acid defined for $R^1$ and
where $R^{2b}$ is an alkyl residue having 1 to 6 carbon atoms, preferably methyl, ethyl, propyl or isopropyl, particularly preferably methyl,
where c=1 to 3 and d=1 to 3
with the proviso that c+d=4.

Liquid imidazolinium salts contained in the formulation according to the invention are preferably 1-alkylamidoimidazolinium and 1-alkoxyalkylimidazolinium salts of general formulae (II) and (III)

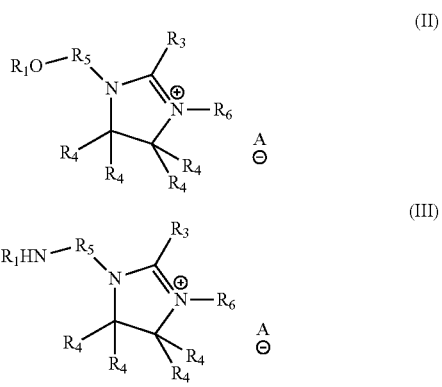

where
$R_3$ is an optionally branched, optionally unsaturated alkyl residue having 1 to 30 carbon atoms optionally interrupted by oxygen atoms,
$R_4$ are each independently hydrogen or alkyl, preferably butyl, propyl, ethyl, methyl or hydrogen,
$R_5$ is a divalent, saturated or unsaturated, straight-chain, branched or cyclic, optionally substituted hydrocarbon residue and optionally interrupted by oxygen atoms, nitrogen atoms or carboxyl groups, preferably ethylene,
$R_6$ is hydrogen or an optionally branched, optionally unsaturated alkyl residue, optionally comprising oxygen atoms or nitrogen atoms, having 1 to 30 carbon atoms, preferably having 1 to 12 carbon atoms, particularly preferably having 1 to 4 carbon atoms, especially preferably ethyl or methyl, and A is a counterion to the positive charges on the quaternary nitrogen groups.

The formulations therefore preferably comprise as component A) a mixture of at least one compound of general formula I) and at least one compound of general formula Ia), as arises, for example, when using technical-grade fatty acid cuts which have longer or shorter acyl residues than defined above for $R^1$ and/or one compound of general formula II) or III).

The compounds of the general formula I) preferably constitute at least 30% by weight, preferably at least 50% by weight, particularly preferably at least 75% by weight, based on all of the compounds of general formula I) and Ia).

Very particular preference is given to mixtures which are obtained if the mixture used is mixed plant oils with a carbon chain distribution for which the following applies:

| Chain length of $R^1$ or $R^{1a}$ (' = number of double bond(s)) | Proportion based on the overall mixture |
|---|---|
| <C 16 | 0-2% by weight |
| C 16 | 4-7% by weight |
| C 16' | 0-2% by weight |
| C 18 | 0-4% by weight |
| C 18' | 55-65% by weight |
| C 18" | 15-25% by weight |
| C 18''' | 6-12% by weight |
| >C 18 | 0-4% by weight |

The compounds of general formula I) where $R^1$=the acyl residue of oleic acid preferably constitute at least 40% by weight, particularly preferably at least 55% by weight, based on all compounds of general formula I) and Ia).

The compounds of general formula I) where $R^1$=the acyl residue of a C16 acid preferably constitute at most 20% by weight, particularly preferably at most 11% by weight, based on all compounds of general formula I) and Ia).

Preferred formulations of this embodiment comprise compounds of general formula I) or Ia) where a=b=c=d=2.

Formulations preferred according to the invention, in particular those for treating keratin fibres, in particular human hair, comprise 0.1 to 7% by weight, preferably 0.2 to 5% by weight and particularly preferably 0.3 to 3% by weight of component A), wherein the percentages by weight refer to the overall formulation.

Particularly good results can be achieved at the predefined concentrations of 0.2 to 2% by weight. The application of the formulations according to the invention to keratin fibres, in particular to human hair, however, is not limited to the use of the active ingredients in low concentration. It is also possible to use concentrated formulations according to the invention in which the predefined concentrations are 2 to 20% by weight or 3 to 14% by weight, in particular 5 to 12% by weight.

The substance group of the polymeric thickeners comprises the natural thickeners such as starch, gelatin, alginates, modified natural products such as cellulose ether or hydroxyethylcellulose, and the fully synthetic polymers, for example, polyacrylates or polyacrylamides and also so-called HEUR=nonionic hydrophobically modified ethoxylated urethanes, also known as associative polyurethane thickeners. These polymers comprise at least two hydrocarbon-based lipophilic polymer chains, which are based on 6 to 30 carbon atoms and are bridged by a hydrophilic unit. Examples of such polyurethane thickeners are PEG-150/stearyl alcohol/SDMI copolymer, PEG-150/decyl alcohol/SMDI copolymer, bis-stearyl PEG/PPG-8/6 SMDI/PEG-400 copolymer and polyether-urea-polyurethanes. Substances of this kind are commercially available under the following product names SERAD FX1010, SERAD FX1100 and SERAD FX1035 (commercially available from Hüls America), RHEOLATE 255, RHEOLATE 278 and RHEOLATE 244 (commercially available from Elementis), DW 1206F, DW 1206J, DW 1206B, DW 1206G, and ACRYSOL RM 2020.

Further polymeric thickeners are known based on (phyllo) silicates or modified aluminas such as bentonites or hectorites or derivatives thereof.

The polymer thickeners which can be used in the formulation according to the invention (component B) are therefore, for example, cellulose, xanthan, carrageenan, galactomannans, guar, tara, cassia, sesbania, locust bean gum, gellan gum, welan gum, carob seed flour, guar seed flour, starch, pectin, lanolin, agar-agar, tragacanth, polysaccharides (e.g., isolated from algae, bacteria or fungi and those listed in "Ullmanns Encyklopädie der technischen Chemie", Vol. 19, Verlag Chemie Weinheim, 1980, pp. 233-263), alginates, carrageenan, gellan, pullulan, scleroglucan, schizophyllan, curdlan, diutan, dextran, welan, chitin, and derivatives thereof, particularly derivatives in the form of alkylations (e.g., methyl ethers, ethyl ethers, C12-18 alkyl ethers), hydroxyalkylations (hydroxyethyl, hydroxypropyl or mixed ethers) and carboxymethylation. Preferred derivatives are starch derivatives, for example, hydroxypropyl starch phosphate, commercially available under the name Structure XL (Akzo Nobel). Furthermore, fully synthetic polymers can be used in the formulations according to the invention such as polyacrylate-based thickeners, polyacrylamide thickeners, for example, cross-linked copolymers (polacrylamides/C13-14 isoparaffin/laureth 7) (acrylamide/sodium acryloyldimethyl taurate copolymer/isohexadecane/polysorbate 80), or linear, amorphous sulphonated polyester, for example, polyester-4.

Moreover, cationic/cationized polymers can also be used, e.g., guar quats, for example, guar hydroxypropyltrimonium chloride, lanolin quats, quaternary derivatives of hydroxyethylcellulose, for example, HEC cocodimonium chloride, hydrolysed proteins, for example, hydroxypropyltrimonium hydrolysed wheat protein or cassia hydroxypropyltrimonium chloride, or polyquaternium polymers, for example, polyquaternium-2, polyquaternium-4, polyquaternium-6, polyquaternium-7, polyquaternium-10, polyquaternium-20, polyquaternium-22, polyquaternium-24, polyquaternium-37, polyquaternium-39, polyquaternium-47, polyquaternium-53, polyquaternium-59, polyquaternium-67, polyquaternium-70, polyquaternium-72 or polyquaternium-74.

Generally, it is also possible to use mixtures of various polymer thickeners.

Particularly preferred formulations according to the invention comprise as polymer thickener at least one selected from the group of polyacrylate-based thickeners, e.g., the so-called carbomers. Carbomers are polymers of acrylic acid or copolymers of C10-30-alkylacrylates and one or more monomers of acrylic acid, methacrylic acid or esters thereof, which have been cross-linked, e.g., with an allyl ether of sucrose or an allyl ether of pentaerythritol.

In particular, the polyacrylate-based thickeners are selected from polymers based on at least one of the following monomers: acrylic acid and salts thereof, methacrylic acid and salts thereof, alkyl esters of acrylic acid and methacrylic acid (e.g., C2-C30), hydroxyethyl acrylate, acrylamide, 2-acrylamido-2-methylpropanesulphonic acid and salts thereof (AMPS). In particular, the polyacrylate-based thickeners are products with INCI designations selected from carbomers, sodium carbomers, acrylates/C10-C30 alkyl acrylate crosspolymer, sodium acrylates/beheneth-25 methacrylate, acrylates/C12-24 pareth-25 acrylate copolymer, acrylates/steareth-20 methacrylate copolymer, acrylates/beheneth-25 methacrylate copolymer, acrylates/steareth-20 itaconate copolymer, acrylates/aminoacrylates/C10-30 alkyl PEG-20 itaconate copolymer, acrylates copolymer, acrylates crosspolymer-4, ammonium acrylates copolymer, polyacrylate-1 crosspolymer, acrylamide/sodium acryloyldimethyl taurate copolymer, sodium acrylate/sodium acryloyldimethyl taurate copolymer, acrylic acid/vinyl pyrrolidone, acrylates/vinyl neodecanoate crosspolymer, polyacrylamide/C13-C14 isoparaffin/laureth-7, acrylamide/sodium acryloyldimethyl taurate polymer/isohexadecane/polysorbate 80 or sodium acrylate/acryloyldimethyl taurate/dimethylacrylamide crosspolymer. Examples of polyacrylate thickeners are polyacrylates from the group of the so-called carbopols, for example, carbopols of the types 980, 981, 1382, 2020, 2984, 3128, 5984 and pemulen TR1, TR2, in each case individually or in combination.

The formulation according to the invention preferably comprises the polymer thickener in an amount of 0.005% by weight to 2% by weight, preferably 0.01% by weight to 0.5% by weight, particularly preferably 0.05% by weight to 0.1% by weight, based on the overall formulation.

Preferred formulations according to the invention are emulsions, preferably oil-in-water emulsions, particularly preferably emulsions in which the oil phase is solid at 25° C., such that an oil-in-water suspension is present at 25° C.

It has proven to be advantageous if the formulations according to the invention additionally comprise at least one fatty alcohol (component C)).

Fatty alcohol in this context is preferably understood as meaning an unbranched or branched monoalcohol with an alkyl group of 8 to 30 carbon atoms, which may also be unsaturated. Preferred fatty alcohols are octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol, and mixtures thereof, in particular technical-grade mixtures, preferably technical-grade coconut or tallow fatty alcohols having 12 to 18, preferably having 16 to 18, carbon atoms, as well as the monounsaturated fatty alcohols, such as oleyl alcohol, elaidyl alcohol, delta-9-cis-hexadecenol, delta-9-octadecenol, trans-delta-9-octadecenol, cis-delta-11-octadecenol, trans-10,cis-12-hexadecadien-1-ol, octacosa-10,19-dien-1-ol and polyunsaturated fatty alcohols such as e.g. linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), with mixtures of coconut or tallow fatty alcohols having 16 to 18 carbon atoms being particularly preferred.

Component C) preferably comprises at least one fatty alcohol having a melting point of greater than 25° C., particularly preferably greater than 50° C., at 1 bar pressure.

The fatty alcohol is preferably present in an amount of 0.5 to 20% by weight, preferably 1 to 10% by weight, particularly 2 to 7% by weight, where the percentages by weight refer to the overall formulation.

Preferred formulations according to the invention are characterized in that component A) is present in an amount of 0.1 to 7% by weight, preferably 0.2 to 5% by weight and particularly preferably 0.3 to 3% by weight, component B) is present in an amount of 0.005% by weight to 2% by weight, preferably 0.01% by weight to 0.5% by weight, particularly preferably 0.05% by weight to 0.1% by weight, based on the overall formulation, and component C) is present in an amount of 0.5 to 20% by weight, preferably 1 to 10% by weight, particularly 2 to 7% by weight, based on the overall formulation.

In a particularly preferred alternative embodiment, component B is selected from the associative polyurethane thickeners and the formulation does not comprise component C), and is therefore free of fatty alcohol. In this context, the preferred associative polyurethane thickeners are those which comprise at least two hydrocarbon-based lipohilic polymer chains, which are based on 6 to 30 carbon atoms and are bridged by a hydrophilic unit. Examples of such polyurethane thickeners are PEG-150/stearyl alcohol/SDMI copolymer, PEG-150/decyl alcohol/SMDI copolymer, bis-stearyl PEG/PPG-8/6 SMDI/PEG-400 copolymer and polyether-urea-polyurethanes. Substances of this kind are commercially available under the following product names SERAD FX1010, SERAD FX1100 and SERAD FX1035, RHEOLATE 255, RHEOLATE 278 and RHEOLATE 244, DW 1206F, DW 1206J, DW 1206B, DW 1206G, and ACRYSOL RM 2020.

The formulations according to the invention preferably include this alternative embodiment component A) in an amount of 0.1 to 7% by weight, preferably 0.2 to 5% by weight and particularly preferably 0.3 to 3% by weight, and component B) in an amount of 0.005% by weight to 30% by weight, preferably 0.5% by weight to 15% by weight, particularly preferably 1% by weight to 5% by weight, based on the total formulation.

It has proven to be advantageous if the formulations according to the invention additionally comprise at least one emulsifier (component D)), preferably in an amount of 0.1 to 10% by weight, preferably 0.25 to 5% by weight, particularly 0.5 to 2.5% by weight, where the percentages by weight refer to the overall formulation.

Emulsifiers preferred in this context are selected from the group of fatty alcohol alkoxylates, in particular the fatty alcohol ethoxylates. Particularly preferred fatty alcohol ethoxylates present are selected from the group comprising polyoxyethylene ethers of lauryl alcohol, CAS number 9002-92-0, macrogol lauryl ether, e.g., polyoxyethylene (4) lauryl ether (Laureth-4, INCI), polyoxyethylene (9) lauryl ether Laureth-9 (INCI),
polyoxyethylene (23) lauryl ether Laureth-23 (INCI)
polyoxyethylene ethers of cetyl alcohol, CAS number 9004-95-9, e.g.,
polyoxyethylene (2) cetyl ether Ceteth-2 (INCI),
polyoxyethylene (10) cetyl ether Ceteth-10 (INCI),
polyoxyethylene (20) cetyl ether Ceteth-20 (INCI),
polyoxyethylene ethers of cetylstearyl alcohol, CAS number 68439-49-6, e.g.,
polyoxyethylene (6) cetylstearyl ether Ceteareth-6 (INCI),
polyoxyethylene (20) cetylstearyl ether Ceteareth-20 (INCI),
polyoxyethylene (25) cetylstearyl ether Ceteareth-25 (INCI),
polyoxyethylene ethers of stearyl alcohol, CAS number 9005-00-9, e.g., polyoxyethylene (2) stearyl ether Steareth-2 (INCI),
polyoxyethylene (10) stearyl ether Steareth-10 (INCI),
polyoxyethylene (20) stearyl ether Steareth-20 (INCI),
polyoxyethylene ethers of oleyl alcohol, CAS number 9004-98-2, e.g.,
polyoxyethylene (2) oleyl ether Oleth-2 (INCI),
polyoxyethylene (10) oleyl ether Oleth-10 (INCI),
polyoxyethylene (20) oleyl ether Oleth-20 (INCI),
or
polyoxyethylene (10) tridecyl ether (CAS number 24938-91-8) and Trideceth-10 (INCI).

Alternatively preferred emulsifiers are selected from the group of polyol esters, in particular the glycerol esters and polyglycerol esters, in particular the polyglycerol esters. Preferably present (poly)glycerol esters are characterized in that they are partial esters. Particularly preferred polyglycerol partial esters are selected from the group comprising polyglycerol partial esters as described in EP-B-0 835 862, which are obtainable by esterification of a polyglycerol mixture with a degree of esterification of the polyglycerol between 30 and 75% and saturated or unsaturated, linear or branched fatty acids with 12 to 22 carbon atoms and dimer fatty acids with an average functionality of 2 to 2.4, esters of citric acid such as, for example, the O/W emulsifier glyceryl stearate citrate, (2-hydroxy-1,2,3-propanetricarboxylic acid-1,2,3-propanetriol monooctadecanoate, INCI Glyceryl Stearate Citrate, CAS 39175-72-9), the citric acid ester of glyceryl stearate, commercially available inter alia under the name AXOL C 62, glyceryl stearate citrate as described in WO2006034992 and WO2008092676 and glyceryl oleate citrate as described in WO2004112731, likewise simple polyglycerol esters, such as, for example, polygylcerol-3 distearate, polyglyceryl-10 stearate, polyglyceryl-6 distearate, mixed esters of polyglycerol and methyl glucose and stearic acid, such as, for example, polyglyceryl-3 methyl glucose distearate and (poly)glycerol partial esters with one or more carboxylic acids having 10 to 24 carbon atoms and residues of a polyfunctional carboxylic acid.

In principle, sorbitan or sucrose esters can also be used as polyol esters. A customary combination is, for example, Sorbitan Stearate & Sucrose Cocoate.

Emulsifiers preferably present in a further alternative are selected from the group of modified siloxanes, for example, those which also carry polyethers besides aliphatic groups based on alpha-olefins. Siloxane-based emulsifiers for oil-in-water emulsions must have a hydrophilic character, for which reason they are generally pure polyether siloxanes. Particularly suitable examples are relatively hydrophobic polyether siloxanes as described in EP1125574, high molecular weight polyether siloxanes as described in EP2168564 and organomodified siloxane block copolymers as described in WO2009138306. Preferably present modified siloxanes are characterized in that they have a HLB value >8. Particularly preferred modified siloxanes are selected from the group comprising Bis-PEG/PPG-16/16 Dimethicone, PEG/PPG-16/16 Dimethicone, Bis-PEG/PPG-20/5 PEG/PPG-20/5 Dimethicone and Methoxy PEG/PPG-25/4 Dimethicone.

In connection with the present invention, the aforementioned emulsifiers produce particularly storage-stable formulations.

It is particularly advantageous and preferable if emulsifiers are present as component D) having a melting point of 60° C. or less at 1 bar, preferably 40° C. and less, particularly preferably 25° C. or less, and particularly preferably 10° C. or less. Fatty alcohols are not emulsifiers in the context of the present invention.

Preferred formulations according to the invention are characterized in that
component A) is present in an amount of 0.1 to 7% by weight, preferably 0.2 to 5% by weight and particularly preferably 0.3 to 3% by weight,
component B) is present in an amount of 0.005% by weight to 2% by weight, preferably 0.01% by weight to 0.5% by weight, particularly preferably 0.05% by weight to 0.1% by weight, based on the overall formulation,
component C) is present in an amount of 0.5 to 20% by weight, preferably 1 to 10% by weight, particularly 2 to 7% by weight, and
component D) is present in an amount of 0.1 to 10% by weight, preferably 0.25 to 5% by weight, particularly 0.5 to 2.5% by weight, based in each case on the overall formulation.

A preferred alternative embodiment may be prepared cold, i.e., it only comprises components which can be processed without melting.

These formulations according to the invention are characterized in that all resulting ester quats, imidazolinium salts, fatty alcohols and emulsifiers have a melting point of 60° C. or less, preferably 40° C. and less, particularly preferably 25° C. or less, and especially preferably 10° C. or less at 1 bar, where in the case that more than one ester quat, imidazolinium salt, fatty alcohol or emulsifier is present, the melting point refers to the mixture of all ester quats, imidazolinium salts, fatty alcohols or emulsifiers in each case.

The formulations according to the invention can comprise e.g. at least one further additional component selected from the group of
emollients,
coemulsifiers,
thickeners/viscosity regulators/stabilizers,
antioxidants,
hydrotropes (or polyols),
solids and fillers,
pearlescence additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts of these components used, reference is made expressly to the relevant handbooks known to the person skilled in the art, e.g. K. Schrader, "Grundlagen and Rezepturen der Kosmetika [Fundamentals and Formulations of Cosmetics]", 2nd edition, pages 329 to 341, Hüthig Buch Verlag Heidelberg.

The amounts of the particular additives are governed by the intended use. Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

It is preferred according to the invention if the formulation has a pH from 3.0 to 5.5, preferably 3.5 to 5.0.

The charge of the ester quats present in the formulation according to the invention must be compensated by corresponding anions; this takes place by means of counteranions present in the formulation according to the invention. Suitable as such counteranions are, for example, the halides, pseudohalides, anions of mineral acids, sulphates, sulphites, hydrogensulphites, sulphonate, alkyl and arylsulphonates, phosphate, hydrogenphosphates, phosphites, hydrogenphosphites, phosphonites, carboxylates, borates, carbonates, sulphides, hydrogensulphides, lactate, glycolate, formate, acetate and propionate.

These anions are preferably selected from those which are suitable for cosmetic application and are therefore for example nontoxic. Particularly preferably, at least one counteranion to the ester quat is present, selected from the group comprising chloride, bromide, iodide, alkyl sulphate, e.g., methyl sulphate, ethyl sulphate, alkylsulphonate, e.g., methylsulphonate, triflate, tosylate, phosphate, sulphate, hydrogensulphate, lactate, glycolate, acetate and citrate, preferably chloride and methyl sulphate.

The formulations according to the invention can be used according to the invention for treating keratin fibres, in particular for treating hair.

The use according to the invention leads to the improvement in the conditioning, shine, flexibility, elasticity and/or combability, and also to a reduction in the probability of breakage of the treated fibres and, moreover, it reduces the antistatic forces between the fibres.

The use according to the invention leads to the protection of the fibres against heat.

The present invention is described in exemplary fashion in the examples cited below, without the invention, the scope of application of which results from the whole of the description and the claims, being limited to the embodiments mentioned in the examples.

EXAMPLES

Synthesis Example 1: Preparation of "1-propanaminium, 2-hydroxy-N-(2-hydroxypropyl)-N,N-dimethyl, Diester with Mixed Plant Oil Fatty Acid, Methyl Sulphate" (According to the Invention)

1120 g (4 mol) of mixed plant oil fatty acid were mixed with 302 g (2.05 mol) of methyldiisopropanolamine and heated to 180° C. with stirring. Water of reaction was distilled off continuously. After the majority of water of reaction has distilled at atmospheric pressure, vacuum was applied and the acid number of the reaction mixture was reacted down to <7 mg KOH/g. The resulting ester amine was cooled to 60° C. and admixed in portions with 240 g (1.90 mol) of dimethyl sulphate, such that the reaction temperature did not exceed 100° C.

After cooling to room temperature, the total amine number (TAN) and the active content of the finished product were analysed.

TAN=5.0 mg KOH/g; active content 1.27 meq/g (cationic active content according to Epton).

Synthesis Example 3: Preparation of "1-propanaminium, 2-hydroxy-N-(2-hydroxypropyl)-N,N-dimethyl, Diester with Tall Oil Fatty Acid, Methyl Sulphate" (According to the Invention)

814 g (2.84 mol) of tall oil fatty acid were mixed with 214 g (1.46 mol) of methyldiisopropanolamine and esterified as described under Example 1. The ester amine had an acid number of 3.2 mg KOH/g. This mixture was alkylated with 168 g (1.33 mol) of dimethyl sulphate as described in example 1. The TAN of the finished product was determined with 7.3 mg KOH/g, the active content was 1.24 meq/g.

Synthesis Example 4: Preparation of "1-propanaminium, 2-hydroxy-N-(2-hydroxypropyl)-N,N-dimethyl, Diester with Erucic Acid, Methyl Sulphate" (According to the Invention)

392 g (1.15 mol) of erucic acid were mixed with 99.3 g (0.68 mol) of methyldiisopropanolamine and esterified as described under example 1. The ester amine had an acid number of 2.2 mg KOH/g. This mixture was alkylated with 72.2 g (0.57 mol) of dimethyl sulphate as described in example 1. The TAN of the finished product was determined with 4.6 mg KOH/g, the active content was 1.45 meq/g.

Synthesis Example 5: Preparation of "1-propanaminium, 2-hydroxy-N-(2-hydroxypropyl)-N,N-dimethyl, Diester with Isostearic Acid, Methyl Sulphate" (According to the Invention)

1017 g (3.5 mol) of isostearic acid (technical-grade quality) were admixed with 262 g (1.79 mol) of methyldiisopropanolamine and esterified as described under Example 1. The ester amine had an acid number of 3.4 mg KOH/g. This mixture was alkylated with 209 g (1.66 mol) of dimethyl sulphate as described in example 1.

The TAN of the finished product was determined with 5.1 mg KOH/g, the active content was 1.26 meq/g.

Synthesis Example 6: General Preparation Procedure of an Imidazolinium Salt without Intermediate Product Isolation (Formula II)

1.75 mol of aminoethylethanolamine (AEEA) and 0.01 mol of 30% Na-methylate were charged in a 4-necked glass flask under N2. 1 mole of the respective carboxylic ester were added at 70° C. with weak exothermicity over 1.5 h, wherein the temperature did not exceed 90° C. The amidation occurred over 6 to 10 h. In order to check this, an IR spectrum was recorded at 1740 nm. A sufficient alkalinity (>2 mg KOH/g) must be ensured. Following the amidation, the alkalinity was neutralized by means of 85% phosphoric acid and the mixture subsequently heated under methanol/ethanol distillation (column) to 175° C. for the cyclization. A vacuum was applied and adjusted to 60 mbar over 3 h, wherein the water of reaction distilled off. Checking was performed by means of an IR spectrum at 1600 and 1650 nm. After cyclization, the excess AEEA was distilled off at reduced pressure at <20 mbar and 175° C. The analytical check was carried out via TAN (total amine number) and TAN (tertiary amine number). The mixture was then cooled to 50° C. and 0.99 mol of the alkylating agent was slowly added dropwise. The course of the reaction was checked by means of the amine number. After 1 to 24 h, the reaction was completed. The remaining residue can be used directly according to the invention without further work-up, depending on the field of application, or be purified by purification methods known to those skilled in the art.

Synthesis Example 7: 1-Ethyl-2-oleyl-3-oleylamido imidazolinium ethyl sulphate 1138 g (4.08 mol) of technical grade oleic acid were charged in a flask equipped with stirrer and distillation column and admixed with 210.4 g (2.04 mol) of diethylenetriamine (DETA). The reaction mixture was heated to 160° C. and the water of reaction was continuously distilled off. If the acid number (AN) fell below 8 mg KOH/g, the reaction temperature was increased to 180-200° C. and the cyclization to the imidazoline was carried out under reduced pressure. If a degree of cyclization of >90% was achieved (determined by: tertiary amine number*100/total amine number), the reaction mixture was cooled to 65° C. and treated in protions with 293 g (1.90 mol) of diethyl sulphate, such that the reaction temperature was maintained in a range of 65-90° C. The imidazoline quat had a total amine number (TAN) of 4.0 mg KOH/g and a cationic activity content (according to Epton) of 1.33 meq/g.

Technical Application Example 1: Stability of the Formulation Example (FE)

TABLE 1b

Stability of the formulation examples

| Formulation Example | Viscosity Brookfield Day 1 | Stability after 3 months RT | Stability after 6 months RT | Stability after 9 months RT | Stability after 3 months 45° C. |
|---|---|---|---|---|---|
| 1 (no polymer thickener) | – | – | –– | Phase separation | Phase separation |
| 2 (with polymer thickener) | + | + | + | + | + |
| 3 (with polymer thickener) | + | + | + | + | + |
| 4 (with polymer thickener) | + | + | + | + | + |
| 5 (with polymer thickener) | + | + | + | + | + |
| 6 (with polymer thickener) | + | + | + | + | + |
| 7 (with polymer thickener) | + | + | + | + | + |
| 8 (with polymer thickener) | + | + | + | + | + |

TABLE 1a

Overview of stability tests for the formulation examples

| | FE 1 | FE 2 | FE 3 | FE 4 | FE 5 | FE 6 | FE 7 | FE 8 | FE 9 |
|---|---|---|---|---|---|---|---|---|---|
| TEGO ® Alkanol 1618, Evonik Industries AG (INCI: Cetearyl Alcohol) | 5.0% | 5.0% | 5.0% | 5.0% | 5.0% | 5.0% | 5.0% | 5.0% | 5.0% |
| TEGINACID ® C, Evonik Industries AG (INCI: Ceteareth-25) | 0.5% | 0.5% | 0.5% | 0.5% | 0.5% | 0.5% | 0.5% | 0.5% | 0.5% |
| Synthesis example 1 | 1.0% | 1.0% | 1.0% | 1.0% | 1.0% | 1.0% | 1.0% | 1.0% | 1.0% |
| Oxynex ® LM | 0.1% | 0.1% | 0.1% | 0.1% | 0.1% | 0.1% | 0.1% | 0.1% | 0.1% |
| Water | to 100% | to 100% | to 100% | to 100% | to 100% | to 100% | to 100% | to 100% | to 100% |
| Preservative, Perfume | q.s. | q.s. | q.s. | q.s. | q.s. | q.s. | q.s. | q.s. | q.s. |
| TEGO ® Carbomer 841 SER (Acrylates/C10-30 Alkyl Acrylate Crosspolymer) | | 0.05% | | | | | | | |
| TEGO ® Carbomer 750 HD (Acrylates/C10-30 Alkyl Acrylate Crosspolymer) | | | 0.05% | | | | | | |
| TEGO ® Carbomer 341 ER (Acrylates/C10-30 Alkyl Acrylate Crosspolymer) | | | | 0.05% | | | | | |
| TEGO ® Carbomer 141 (Carbomer) | | | | | 0.05% | | | | |
| Carrageen | | | | | | 0.05% | | 0.025% | |
| Xanthan gum | | | | | | | 0.05% | 0.025% | |
| Hydroxyethylcellulose | | | | | | | | | 0.05% |

TABLE 1b-continued

Stability of the formulation examples

| Formulation Example | Viscosity Brookfield Day 1 | Stability after 3 months RT | Stability after 6 months RT | Stability after 9 months RT | Stability after 3 months 45° C. |
|---|---|---|---|---|---|
| 9 (with polymer thickener) | + | + | + | + | + |
| 56 (no polymer thickener) | - | - | -- | -- | Phase separation |
| 57 (with polymer thickener) | + | + | + | + | + |
| 60 (with polymer thickener) | + | + | + | + | + |

-- = <2000 mPas
- = >2000 mPas < 7000 mPas
o = >7000 < 10000 mPas
+ = >10000 mPas

The formulation samples were stored at room temperature or 45° C. The viscosities were determined using a Brookfield viscometer type LV-DV-I+ or LV-DV-II+.

The measurement was conducted at 25° C. (+/−0.5° C.). For the measurement, 100 ml powder flasks were filled; equilibrated and measured free of air bubbles. Prior to the measurement, the viscometer was calibrated without spindle by pressing the "auto range" key. The course of the calibration is shown on the display. After completion of the calibration, a spindle corresponding to the expected viscosity was mounted on the viscometer. The spindle number was input into the device. To determine the viscosity, the viscometer was positioned relative to the sample such that the spindle dipped into the product up to the mark. The measurement was triggered by means of the start key. The measurement should be conducted in the favourable measurement range of 50% (+/−20%) of the maximum measureable torque. This can be adjusted by changing the rotational speed/spindle number.

The result of the measurement is given on the viscometer display in mPas.

Technical Application Example 2: Application Technology of Hair Treatment Compositions for Assessing the Effect of the Thickener on the Sensory Properties of the Formulations For the applications-related assessment, hair tresses were used which had been predamaged in a standardized manner by means of a bleaching treatment. For this purpose, standard hairdressing products were used. The damage to the hair tresses is described in detail in DE10327871.

For the applications-related assessment, example formulation 1 comprising no polymeric thickener was compared with example formulations 2-5, which additionally comprise a polymeric thickener.

The composition of the test formulations was deliberately chosen to be simple in order to avoid the test results being influenced by (normally present) formulation constituents. Besides the specified ingredients and/or instead of the specified ingredients, formulations according to the invention can also comprise further ingredients. In particular, the combination with further ingredients can lead to a synergistic improvement in the case of the described effects.

The hair is pretreated with a shampoo formulation (Table 1), which contains no conditioner.

TABLE 2

Shampoo formulation for the pretreatment of the hair tresses.

| Texapon NSO ®, 28% strength, Cognis (INCI: SodiumLaureth Sulphate) | 42.9% |
|---|---|
| NaCl | 3% |
| Water, demineralized | ad 100.0 |

Standardized treatment of predamaged hair tresses with conditioning samples: The hair tresses predamaged as described above were washed with the shampoo formulation from Table 2.

Here, the hair tresses were wetted under running warm water. The excess water was gently squeezed out by hand, then the shampoo was applied and worked gently into the hair for 1 min (0.5 ml/2 g hair tress). The hair tress was rinsed for 30 s under running warm water. This procedure is repeated once more except that final rinsing was for 1 min. Then, directly after washing, the hair tresses were conditioned with formulation examples 1-5.

Here, the rinse was applied and gently worked into the hair (0.5 ml/2 g hair tress). After a residence time of 1 min, the hair was rinsed for a) 1 min or for b) 3 min Before the sensory assessment, the hair was dried for at least 12 h in the air at 50% humidity and 25° C.

Assessment criteria:

The sensory evaluations were made using grades awarded on a scale from 1 to 5, with 1 being the worst evaluation and 5 being the best evaluation. The individual test criteria each contain their own evaluation.

The test criteria were:

Wet combability, wet feel, dry combability, dry feel.

a) 1 min rinsing time

TABLE 3a

Results of the conditioning of hair with 1 min rinsing time

| | Wet combability | Wet feel | Dry combability | Dry feel |
|---|---|---|---|---|
| Formulation Example 1 | 5 | 5 | 5 | 5 |
| Formulation Example 2 | 5 | 5 | 5 | 5 |
| Formulation Example 3 | 5 | 5 | 5 | 5 |
| Formulation Example 4 | 5 | 5 | 5 | 5 |
| Formulation Example 5 | 5 | 5 | 5 | 5 | b) 3 min rinsing time

TABLE 3b

Results of the conditioning of hair with 3 min rinsing time

| | Wet combability | Wet feel | Dry combability | Dry feel |
|---|---|---|---|---|
| Formulation Example 1 | 5 | 5 | 5 | 5 |
| Formulation Example 2 | 5 | 5 | 5 | 5 |
| Formulation Example 3 | 5 | 5 | 5 | 5 |
| Formulation Example 4 | 5 | 5 | 5 | 5 |
| Formulation Example 5 | 5 | 5 | 5 | 5 |

The results in Tables 3a and 3b show that the improved stability of the formulations do not negatively influence the excellent hair conditioning.

Formulation Example 1 (not According to the Invention)

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| Water | 93.4% |
| Preservative, Perfume | q.s. |

Formulation Example 2

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| TEGO ® Carbomer 841 SER (Acrylates/C10-30 Alkyl Acrylate Crosspolymer) | 0.05% |
| Water | 93.35% |
| Preservative, Perfume | q.s. |

Formulation Example 3

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| TEGO ® Carbomer 750 HD (Acrylates/C10-30 Alkyl Acrylate Crosspolymer) | 0.05% |
| Water | 93.35% |
| Preservative, Perfume | q.s. |

Formulation Example 4

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| TEGO ® Carbomer 341 ER (Acrylates/C10-30 Alkyl Acrylate Crosspolymer) | 0.05% |
| Water | 93.35% |
| Preservative, Perfume | q.s. |

Formulation Example 5

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| TEGO ® Carbomer 141 (Carbomer) | 0.05% |
| Water | 93.35% |
| Preservative, Perfume | q.s. |

Formulation Example 6 (not According to the Invention)

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| Carrageen | 0.05% |
| Water | 93.35% |
| Preservative, Perfume | q.s. |

Formulation Example 7

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| Xanthan Gum | 0.05% |
| Water | 93.35% |
| Preservative, Perfume | q.s. |

Formulation Example 8

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| Xanthan Gum | 0.025% |
| Carrageen | 0.025% |
| Water | 93.35% |
| Preservative, Perfume | q.s. |

Formulation Example 9

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 1.0% |
| Synthesis example 1 | 1.0% |
| Oxynex ® LM | 0.1% |
| Hydroxyethylcellulose | 0.1% |
| Propyl Gallate | 0.1% |
| Water | 92.7% |
| Preservative, Perfume | q.s. |

Formulation Example 10

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 1.0% |
| Synthesis example 1 | 1.0% |
| Oxynex ® LM | 0.1% |
| Hydroxyethylcellulose | 0.1% |
| Propyl Gallate | 0.1% |
| TEGIN ® M (Glyceryl Stearate) | 2.0% |
| Water | 90.7% |
| Preservative, Perfume | q.s. |

Formulation Example 11

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 1 | 1.0% |
| Oxynex ® LM | 0.1% |
| TEGO ® Carbomer 341 ER (Acrylates/C10-30 Alkyl Acrylate Crosspolymer) | 0.1% |
| Water | 93.30% |
| Preservative, Perfume | q.s. |

Formulation Example 12 (not According to the Invention)

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| Oxynex ® LM | 0.1% |
| Water | 91.4% |
| Preservative, Perfume | q.s. |

Formulation Example 13

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| TEGO ® Carbomer 841 SER (Acrylates/C10-30 Alkyl Acrylate Crosspolymer) | 0.05% |
| Water | 91.45% |
| Preservative, Perfume | q.s. |

Formulation Example 14

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| TEGO ® Carbomer 750 HD (Acrylates/C10-30 Alkyl Acrylate Crosspolymer) | 0.05% |
| Water | 91.45% |
| Preservative, Perfume | q.s. |

Formulation Example 15

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| TEGO ® Carbomer 341 ER (Acrylates/C10-30 Alkyl Acrylate Crosspolymer) | 0.05% |
| Water | 91.45% |
| Preservative, Perfume | q.s. |

Formulation Example 16

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| TEGO ® Carbomer 141 (Carbomer) | 0.05% |
| Water | 91.45% |
| Preservative, Perfume | q.s. |

Formulation Example 17

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| Carrageen | 0.05% |
| Water | 91.45% |
| Preservative, Perfume | q.s. |

Formulation Example 18

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| Xanthan Gum | 0.1% |
| Water | 91.45% |
| Preservative, Perfume | q.s. |

Formulation Example 19

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |

-continued

| | |
|---|---|
| Xanthan Gum | 0.05% |
| Carrageen | 0.05% |
| Water | 91.45% |
| Preservative, Perfume | q.s. |

Formulation Example 20

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 1 | 1.0% |
| Hydroxyethylcellulose | 0.1% |
| Propyl Gallate | 0.1% |
| Water | 90.8% |
| Preservative, Perfume | q.s. |

Formulation Example 21

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 1 | 1.0% |
| Hydroxyethylcellulose | 0.1% |
| Propyl Gallate | 0.1% |
| TEGIN ® M (Glyceryl Stearate) | 2.0% |
| Water | 88.8% |
| Preservative, Perfume | q.s. |

Formulation Example 22

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 1 | 1.0% |
| TEGO ® Carbomer 341 ER (Acrylates/C10-30 Alkyl Acrylate Crosspolymer) | 0.1% |
| Water | 91.45% |
| Preservative, Perfume | q.s. |

Formulation Example 23 (not According to the Invention)

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| Oxynex ® LM | 0.1% |
| Water | 91.4% |
| Preservative, Perfume | q.s. |

Formulation Example 24

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| TEGO ® Carbomer 841 SER (Acrylates/C10-30 Alkyl Acrylate Crosspolymer) | 0.05% |
| Water | 91.45% |
| Preservative, Perfume | q.s. |

Formulation Example 25

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| TEGO ® Carbomer 750 HD (Acrylates/C10-30 Alkyl Acrylate Crosspolymer) | 0.05% |
| Water | 91.45% |
| Preservative, Perfume | q.s. |

Formulation Example 26

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| TEGO ® Carbomer 341 ER (Acrylates/C10-30 Alkyl Acrylate Crosspolymer) | 0.05% |
| Water | 91.45% |
| Preservative, Perfume | q.s. |

Formulation Example 27

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| TEGO ® Carbomer 141 (Carbomer) | 0.05% |
| Water | 91.45% |
| Preservative, Perfume | q.s. |

Formulation Example 28

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| Carrageen | 0.05% |
| Water | 91.45% |
| Preservative, Perfume | q.s. |

Formulation Example 29

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| Xanthan Gum | 0.1% |
| Water | 91.45% |
| Preservative, Perfume | q.s. |

Formulation Example 30

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| Xanthan Gum | 0.05% |
| Carrageen | 0.05% |
| Water | 91.45% |
| Preservative, Perfume | q.s. |

Formulation Example 31

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 3 | 1.0% |
| Hydroxyethylcellulose | 0.1% |
| Propyl Gallate | 0.1% |
| Water | 90.8% |
| Preservative, Perfume | q.s. |

Formulation Example 32

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 3 | 1.0% |
| Hydroxyethylcellulose | 0.1% |
| Propyl Gallate | 0.1% |
| TEGIN ® M (Glyceryl Stearate) | 2.0% |
| Water | 88.8% |
| Preservative, Perfume | q.s. |

Formulation Example 33

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 3 | 1.0% |
| TEGO ® Carbomer 341 ER (Acrylates/C10-30 Alkyl Acrylate Crosspolymer) | 0.1% |
| Water | 91.45% |
| Preservative, Perfume | q.s. |

Formulation Example 34 (not According to the Invention)

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| Oxynex ® LM | 0.1% |
| Water | 91.4% |
| Preservative, Perfume | q.s. |

Formulation Example 35

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| TEGO ® Carbomer 841 SER (Acrylates/C10-30 Alkyl Acrylate Crosspolymer) | 0.05% |
| Water | 91.45% |
| Preservative, Perfume | q.s. |

Formulation Example 36

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| TEGO ® Carbomer 750 HD (Acrylates/C10-30 Alkyl Acrylate Crosspolymer) | 0.05% |
| Water | 91.45% |
| Preservative, Perfume | q.s. |

Formulation Example 37

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| TEGO ® Carbomer 341 ER (Acrylates/C10-30 Alkyl Acrylate Crosspolymer) | 0.05% |
| Water | 91.45% |
| Preservative, Perfume | q.s. |

Formulation Example 38

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| TEGO ® Carbomer 141 (Carbomer) | 0.05% |
| Water | 91.45% |
| Preservative, Perfume | q.s. |

Formulation Example 39

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| Carrageen | 0.05% |
| Water | 91.45% |
| Preservative, Perfume | q.s. |

Formulation Example 40

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| Xanthan Gum | 0.1% |
| Water | 91.45% |
| Preservative, Perfume | q.s. |

Formulation Example 41

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| Xanthan Gum | 0.05% |
| Carrageen | 0.05% |
| Water | 91.45% |
| Preservative, Perfume | q.s. |

Formulation Example 42

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 4 | 1.0% |
| Hydroxyethylcellulose | 0.1% |
| Propyl Gallate | 0.1% |
| Water | 90.8% |
| Preservative, Perfume | q.s. |

Formulation Example 43

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 4 | 1.0% |
| Hydroxyethylcellulose | 0.1% |
| Propyl Gallate | 0.1% |
| TEGIN ® M (Glyceryl Stearate) | 2.0% |
| Water | 88.8% |
| Preservative, Perfume | q.s. |

Formulation Example 44

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 4 | 1.0% |
| TEGO ® Carbomer 341 ER (Acrylates/C10-30 Alkyl Acrylate Crosspolymer) | 0.1% |
| Water | 91.45% |
| Preservative, Perfume | q.s. |

Formulation Example 45 (not According to the Invention)

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| Oxynex ® LM | 0.1% |
| Water | 91.4% |
| Preservative, Perfume | q.s. |

Formulation Example 46

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| TEGO ® Carbomer 841 SER (Acrylates/C10-30 Alkyl Acrylate Crosspolymer) | 0.05% |
| Water | 91.45% |
| Preservative, Perfume | q.s. |

Formulation Example 47

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| TEGO ® Carbomer 750 HD (Acrylates/C10-30 Alkyl Acrylate Crosspolymer) | 0.05% |
| Water | 91.45% |
| Preservative, Perfume | q.s. |

Formulation Example 48

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| TEGO ® Carbomer 341 ER (Acrylates/C10-30 Alkyl Acrylate Crosspolymer) | 0.05% |
| Water | 91.45% |
| Preservative, Perfume | q.s. |

Formulation Example 49

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| TEGO ® Carbomer 141 (Carbomer) | 0.05% |
| Water | 91.45% |
| Preservative, Perfume | q.s. |

Formulation Example 50

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| Carrageen | 0.05% |
| Water | 91.45% |
| Preservative, Perfume | q.s. |

Formulation Example 51

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| Xanthan Gum | 0.1% |
| Water | 91.45% |
| Preservative, Perfume | q.s. |

Formulation Example 52

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| Xanthan Gum | 0.05% |
| Carrageen | 0.05% |
| Water | 91.45% |
| Preservative, Perfume | q.s. |

Formulation Example 53

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 5 | 1.0% |
| Hydroxyethylcellulose | 0.1% |
| Propyl Gallate | 0.1% |
| Water | 90.8% |
| Preservative, Perfume | q.s. |

Formulation Example 54

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 5 | 1.0% |
| Hydroxyethylcellulose | 0.1% |
| Propyl Gallate | 0.1% |
| TEGIN ® M (Glyceryl Stearate) | 2.0% |
| Water | 88.8% |
| Preservative, Perfume | q.s. |

Formulation Example 55

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 5 | 1.0% |
| TEGO ® Carbomer 341 ER (Acrylates/C10-30 Alkyl Acrylate Crosspolymer) | 0.1% |
| Water | 91.45% |
| Preservative, Perfume | q.s. |

Formulation Example 56 (not According to the Invention)

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 7 | 1.0% |
| Oxynex ® LM | 0.1% |
| Water | 93.4% |
| Preservative, Perfume | q.s. |

Formulation Example 57

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 7 | 1.0% |
| Oxynex ® LM | 0.1% |
| TEGO ® Carbomer 841 SER (Acrylates/C10-30 Alkyl Acrylate Crosspolymer) | 0.05% |
| Water | 93.35% |
| Preservative, Perfume | q.s. |

Formulation Example 58

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 7 | 1.0% |

-continued

| | |
|---|---|
| TEGO ® Carbomer 750 HD (Acrylates/C10-30 Alkyl Acrylate Crosspolymer) | 0.05% |
| Water | 91.45% |
| Preservative, Perfume | q.s. |

Formulation Example 59

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 7 | 1.0% |
| TEGO ® Carbomer 341 ER (Acrylates/C10-30 Alkyl Acrylate Crosspolymer) | 0.05% |
| Water | 91.45% |
| Preservative, Perfume | q.s. |

Formulation Example 60

| | |
|---|---|
| TEGO ® Alkanol 1618, Evonik Industries AG (INCI: Cetearyl Alcohol) | 5.0% |
| TEGINACID ® C, Evonik Industries AG (INCI: Ceteareth-25) | 0.5% |
| Synthesis example 7 | 1.0% |
| TEGO ® Carbomer 141 (Carbomer) | 0.05% |
| Oxynex ® LM | 0.1% |
| Water | 93.35% |
| Preservative, Perfume | q.s. |

Formulation Example 61

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 7 | 1.0% |
| Carrageen | 0.05% |
| Water | 91.45% |
| Preservative, Perfume | q.s. |

Formulation Example 62

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 7 | 1.0% |
| Xanthan Gum | 0.1% |
| Water | 91.45% |
| Preservative, Perfume | q.s. |

Formulation Example 63

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 7 | 1.0% |
| Xanthan Gum | 0.05% |
| Carrageen | 0.05% |
| Water | 91.45% |
| Preservative, Perfume | q.s. |

Formulation Example 64

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 7 | 1.0% |
| Hydroxyethylcellulose | 0.1% |
| Propyl Gallate | 0.1% |
| Water | 90.8% |
| Preservative, Perfume | q.s. |

Formulation Example 65

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 1.0% |
| Synthesis example 7 | 1.0% |
| Hydroxyethylcellulose | 0.1% |
| Propyl Gallate | 0.1% |
| TEGIN ® M (Glyceryl Stearate) | 2.0% |
| Water | 88.8% |
| Preservative, Perfume | q.s. |

Formulation Example 66

| | |
|---|---|
| TEGO ® Alkanol 1618, Evonik Industries AG (INCI: Cetearyl Alcohol) | 7.0% |
| TEGINACID ® C, Evonik Industries AG (INCI: Ceteareth-25) | 0.5% |
| Synthesis example 7 | 1.0% |
| TEGO ® Carbomer 341 ER (Acrylates/C10-30 Alkyl Acrylate Crosspolymer) | 0.1% |
| Water | 91.45% |
| Preservative, Perfume | q.s. |

Formulation Example 67 to 70

| | 67 | 68 | 69 | 70 |
|---|---|---|---|---|
| Aculyn 46N Polymer; DOW (INCI: PEG-150/stearyl alcohol/SDMI copolymer; 19%) | 15.79 | 15.79 | 15.79 | 15.79 |
| Inventive example 1 | 1.5 | 1.5 | 1.5 | 2.0 |
| Oleyl Alcohol (85%) | | 0.50 | | |
| TEGOSOFT ® M, Evonik Nutrition & Care GmbH (INCI: Isopropyl Myristate) | 0.50 | 0.50 | 0.50 | 0.50 |
| TEGO ® Pearl N 100; Evonik Nutrition & Care GmbH (INCI: Glycol Distearate; Steareth-4) | 2.00 | 2.00 | | |

-continued

|  | 67 | 68 | 69 | 70 |
|---|---|---|---|---|
| ABIL ® ME 45; Evonik Nutrition & Care GmbH (INCI Silicone Quaternium-22; Polyglyceryl-3 Caprate; Dipropylene Glycol; Cocamidopropyl Betaine) |  | 1.70 |  |  |
| Perfume | 0.30 | 0.30 | 0.30 | 0.30 |
| Preservative | q.s. | q.s. | q.s. | q.s. |
| Water | 79.91 | 77.71 | 81.97 | 81.41 |

Formulation Example 71 and 72

|  | 71 | 72 |
|---|---|---|
| Aqupec HU C2002; Sumitomo Seika/Presperse (INCI: Bis-Stearyl Peg/PPG-8/6 SMDI/Peg-400 Copolymer) | 1.00 | 0.75 |
| Structure XL; AkzoNobel (INCI: Hydroxypropyl Starch Phosphate) |  | 0.50 |
| Inventive example 1 | 2.00 | 2.00 |
| TEGOSOFT ® OER; Evonik Nutrition & Care GmbH (INCI: Oleyl Erucate) | 1.00 | 1.00 |
| ABIL ® ME 45; Evonik Nutrition & Care GmbH (INCI Silicone Quaternium-22; Polyglyceryl-3 Caprate; Dipropylene Glycol; Cocamidopropyl Betaine) | 1.70 | 1.70 |
| Perfume | 0.30 | 0.30 |
| Preservative | q.s. | q.s. |
| Water | 94.25 | 93.75 |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, by fall within the scope of the appended claims.

What is claimed as new is:

1. A formulation comprising:
A) at least one liquid ester quat, and
B) at least one polymer thickener, wherein the liquid ester quat comprises at least one compound of general formula I)

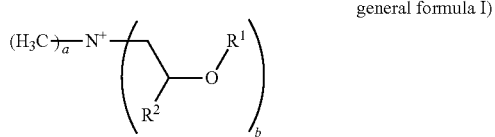

general formula I)

where $R^1$ is an acyl residue of an at least monounsaturated fatty acid having a chain length of 18 to 24 carbon atoms or the acyl residue of isostearic acid or ricinoleic acid, where $R^2$ is an alkyl residue having 1 to 6 carbon atoms, where $a=1$ to 3 and $b=1$ to 3, with the proviso that $a+b=4$.

2. The formulation according to claim 1, further comprising:
at least one compound of general formula Ia)

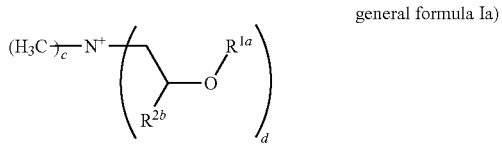

general formula Ia)

where $R^{1a}$ is an acyl residue of a carboxylic acid different from the carboxylic acid defined for $R^1$, wherein $R^1$ is an acyl residue of an at least monounsaturated fatty acid having a chain length of 18 to 24 carbon atoms or the acyl residue of isostearic acid or ricinoleic acid, and where $R^{2b}$ is an alkyl residue having 1 to 6 carbon atoms, where $c=1$ to 3 and $d=1$ to 3
with the proviso that $c+d=4$.

3. The formulation according to claim 1, further comprising a liquid imidazolinium salt, wherein the liquid imidazolinium salt is selected from the group consisting of 1-alkylamidoimidazolinium and 1-alkoxyalkylimidazolinium salts of general formulae (II) and (III)

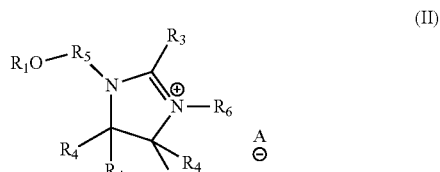

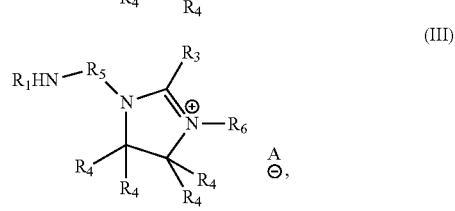

where
$R_3$ is an optionally branched, optionally unsaturated alkyl residue having 1 to 30 carbon atoms optionally interrupted by oxygen atoms,
$R_4$ are each independently hydrogen or alkyl,
$R_5$ is a divalent, saturated or unsaturated, straight-chain, branched or cyclic, optionally substituted hydrocarbon residue and optionally interrupted by oxygen atoms, nitrogen atoms or carboxyl groups,
$R_6$ is hydrogen or an optionally branched, optionally unsaturated alkyl residue, optionally comprising oxygen atoms or nitrogen atoms, having 1 to 30 carbon atoms, and
A is a counterion to the positive charges on the quaternary nitrogen groups.

4. The formulation according to claim 1, wherein component A) is present in an amount of 0.1 to 7% by weight, wherein the percentages by weight refer to the overall formulation.

5. The formulation according to claim 1, wherein the polymer thickener is selected from the group consisting of natural thickeners, modified natural products, and fully synthetic polymers, thickeners based on silicates or modified aluminas or derivatives thereof and cationic/cationized polymers.

6. The formulation according to claim 1, wherein the polymer thickener is selected from the group consisting of polyacrylate-based thickeners.

7. The formulation according to claim 1, wherein component B) is present in an amount of 0.005% by weight to 2% by weight, based on the overall formulation.

8. The formulation according to claim 1, wherein the formulation is an emulsion.

9. The formulation according to claim 1, further comprising:

C) at least one fatty alcohol.

10. The formulation according to claim 9, wherein the fatty alcohol is selected from the group consisting of octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, melissyl alcohol, and mixtures thereof.

11. The formulation according to claim 9, wherein component C) is present in an amount of 0.5 to 20% by weight, based on the overall formulation.

12. The formulation according to claim 9, further comprising:

D) at least one emulsifier.

13. The formulation according to claim 12, wherein component A) is present in an amount of 0.1 to 7% by weight, component B) is present in an amount of 0.005% by weight to 2% by weight, component C) is present in an amount of 0.5 to 20% by weight, and component D) is present in an amount of 0.1 to 10% by weight, based in each case on the overall formulation.

* * * * *